(12) United States Patent
Long

(10) Patent No.: US 7,351,202 B2
(45) Date of Patent: Apr. 1, 2008

(54) MEDICAL DEVICE WITH TRACK AND METHOD OF USE

(75) Inventor: Gary L. Long, Gerards Cross (GB)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 762 days.

(21) Appl. No.: 10/406,020

(22) Filed: Apr. 3, 2003

(65) Prior Publication Data
US 2004/0111020 A1     Jun. 10, 2004

(51) Int. Cl.
*A61B 1/01* (2006.01)
*A61M 25/09* (2006.01)

(52) U.S. Cl. ............... 600/106; 600/104; 600/114; 600/585

(58) Field of Classification Search ........... 600/104, 600/106, 114, 434, 585; 604/164.13, 528
See application file for complete search history.

(56) References Cited

U.S. PATENT DOCUMENTS

| | | | |
|---|---|---|---|
| 4,176,662 A | 12/1979 | Frazer | |
| 4,198,960 A * | 4/1980 | Utsugi | 600/104 |
| 4,207,872 A | 6/1980 | Meiri et al. | |
| 4,326,530 A | 4/1982 | Fleury, Jr. | |
| 4,447,227 A | 5/1984 | Kotsanis | |
| 4,793,326 A * | 12/1988 | Shishido | 356/241.4 |
| 5,263,928 A * | 11/1993 | Trauthen et al. | 604/509 |
| 5,337,732 A | 8/1994 | Grundfest et al. | |
| 5,345,925 A | 9/1994 | Allred, III et al. | |
| 5,398,670 A | 3/1995 | Stubbs et al. | |
| 5,509,900 A * | 4/1996 | Kirkman | 604/104 |
| 5,522,819 A | 6/1996 | Graves et al. | |
| 5,595,565 A | 1/1997 | Trimmer et al. | |
| 5,604,531 A | 2/1997 | Iddan et al. | |
| 5,643,175 A | 7/1997 | Adair | |
| 5,746,692 A * | 5/1998 | Bacich et al. | 600/104 |
| 5,836,947 A | 11/1998 | Fleischmann et al. | |
| 5,895,417 A | 4/1999 | Pomeranz et al. | |
| 5,904,648 A | 5/1999 | Arndt et al. | |
| 5,984,860 A | 11/1999 | Shan | |
| 6,007,482 A | 12/1999 | Madni et al. | |
| 6,036,636 A | 3/2000 | Konomura et al. | |
| 6,123,665 A * | 9/2000 | Kawano | 600/104 |

(Continued)

FOREIGN PATENT DOCUMENTS

EP       0667115 A1     1/1995

(Continued)

OTHER PUBLICATIONS

Technical Advances and Experimental Devices for Enteroscopy pp. 1052-5157, Charles Alendander Mosse, BA, MSC and C. Paul Swain, MD, vol. 9, No. 1, Jan. 1999.

(Continued)

*Primary Examiner*—John P. Leubecker

(57) ABSTRACT

A medical device for performing medical procedures inside a lumen (such as the GI tract) of a patient is provided. The device includes an elongate flexible member which can be advanced along a track. The track can include a loop portion which can be advanced ahead of the elongate flexible member. The distal end of the flexible member can include a camera, light source, vacuum opening, and a working channel for receiving medical instruments.

25 Claims, 11 Drawing Sheets

U.S. PATENT DOCUMENTS

| | | | |
|---|---|---|---|
| 6,162,171 A | 12/2000 | Ng et al. | |
| 6,190,382 B1 | 2/2001 | Ormsby et al. | |
| 6,196,966 B1 * | 3/2001 | Kerin et al. | 600/114 |
| 6,203,525 B1 | 3/2001 | Whayne et al. | |
| 6,428,489 B1 * | 8/2002 | Jacobsen et al. | 600/585 |
| 6,454,758 B1 | 9/2002 | Fleischman et al. | |
| 2004/0084049 A1 * | 5/2004 | Baran | 128/207.14 |

FOREIGN PATENT DOCUMENTS

| | | |
|---|---|---|
| EP | 0827712 A2 | 11/1998 |
| FR | 2.481915 A1 | 11/1981 |
| WO | WO 94/05200 | 3/1994 |
| WO | WO 98/11816 | 3/1998 |
| WO | WO 98/19608 A1 | 5/1998 |
| WO | WO 99/30610 | 6/1999 |
| WO | WO 99/32028 | 7/1999 |
| WO | WO 99/34726 | 7/1999 |
| WO | WO 99/53827 | 10/1999 |
| WO | WO 00/22975 | 4/2000 |
| WO | WO 0044/275 | 8/2000 |
| WO | WO 01/08548 | 2/2001 |
| WO | WO 01/08548 A1 | 2/2001 |

OTHER PUBLICATIONS

EPO Search Reports dated Apr. 6, 2004 for corresponding patent applications, European Patent Application No. 03257644.9-1526- and 03257645.6-1526-.

EPO Communication dated Jun. 7, 2004 for corresponding patent applications, European Patent Application No. 02257750.6.

* cited by examiner

MEDICAL DEVICE WITH TRACK AND METHOD OF USE

This application incorporates by reference and claims priority to U.S. Pat. application Ser. No. 10/310,365 "Locally-Propelled Intraluminal Device with Cable Loop Track and Method of Use" filed Dec. 5, 2002 now U.S. Pat. No. 7,226,410.

FIELD OF THE INVENTION

The present invention relates to a medical device, and more particularly to a medical device that can be advanced along a track located within a lumen of a patient's body.

BACKGROUND

A physician typically accesses and visualizes tissue within a patient's gastrointestinal (GI) tract with a long, flexible endoscope. For the upper GI, a physician may insert a gastroscope into the sedated patient's mouth to examine and treat tissue in the esophagus, stomach, and proximal duodenum. For the lower GI, a physician may insert a colonoscope through the sedated patient's anus to examine the rectum and colon. Some endoscopes have a working channel, typically about 2.5-3.5 mm in diameter, extending from a port in the handpiece to the distal tip of the flexible shaft. A physician may insert medical instruments into the working channel to help diagnose or treat tissues within the patient. Physicians commonly take tissue biopsies from the mucosal lining of the GI tract using a flexible, biopsy forceps through the working channel of the endoscope.

Insertion of a flexible endoscope, especially into the colon, is usually a very time-consuming and uncomfortable procedure for the patient, even when sedated with drugs. A physician often needs several minutes to push a flexible endoscope through the convoluted sigmoid, descending, transverse, and ascending portions of the colon. The physician may diagnose and/or treat tissues within the colon either during insertion or removal of the endoscope. Often the flexible endoscope "loops" within the colon, such as at the sigmoid colon or at the splenic flexure of the colon, so that it becomes difficult to further advance the endoscope along the colon. When a loop is formed, the force exerted to push the scope stretches the mesentery and causes pain for the patient. Depending on the anatomy of the patient and the skill of the physician in manipulating the flexible endoscope, some portions of the colon may be unexamined, thus increasing the risk of undiagnosed disease.

Given® Engineering LTD, Yoqneam, Israel, sells a device in the U.S. called the M2A™ Swallowable Imaging Capsule. The device contains a tiny video camera, battery, and transmitter. It is propelled through the gastrointestinal tract by natural peristalsis. The device is currently used for diagnostic purposes and passes through the intestinal tract with a velocity determined by the natural, peristaltic action of the patient's body. World Publication No. WO 0108548A1 filed by C. Mosse, et al. describes a self-propelling device adapted to travel through a passage having walls containing contractile tissue. The applicants disclose that the device is particularly useful as an enteroscope and may also carry objects such as feeding tubes, guide wires, physiological sensors or conventional endoscopes within the gut. A summary of other alternatives to push endoscopy can be found in "*Technical Advances and Experimental Devices for Enteroscopy*" by C. Mosse, et al, published in *Gastrointestinal Endoscopy Clinics of North America*, Volume 9, Number 1, January 1999: pp. 145-161.

Scientists and Engineers continue to seek improved methods and devices for accessing, diagnosing and/or treating tissue within body lumens, including the GI tract.

SUMMARY OF THE INVENTION

Applicant has recognized the desirability of a low cost, potentially disposable medical device which may provide physicians with a desirable alternative to using a conventional, reusable, flexible endoscope. Eliminating the need for the operator to make constant adjustment of the articulation controls of an endoscope may reduce the skill required to intubate the device, allowing operators other than physicians to use the device. This is advantageous because gastroenterologists currently do not have the capacity to handle all of the patients that need colonoscopies, so equipment that enables other staff, such as nurses, to help with the procedure could increase the capacity and allow gastroenterologists to treat more patients.

In one embodiment, the present invention provides a medical device comprising an elongate flexible member which can be advanced through a body lumen on a track. The track can have a loop portion which is advanced distally of the flexible member, and the member is then advanced along the track. The flexible member can include visualization means, light means, and channels for fluids (gas or liquid) and instruments.

The present invention also provides a method of moving a medical apparatus through a patient's body, such as through the GI tract. The method can comprise the steps of positioning a portion of the medical device within the body lumen; advancing a length of track distally of the medical device; and advancing the medical device on the track to move distally within the lumen. The medical device can be advanced distally while simultaneously retracting a portion of the track proximally.

The invention can be used to assist in diagnosis and treatment of tissue, including the placement of medical instruments (including without limitation balloons, dilators, tissue graspers, tissue cutting devices, tissue stapling devices, tissue staining or treatment devices, vessel ligation devices, and tissue ablation devices) at a desired tissue site.

BRIEF DESCRIPTION OF THE DRAWINGS

While the novel features of the invention are set forth with particularity in the appended claims, the invention in all its embodiments may be more fully understood with reference to the following description and accompanying drawings.

DETAILED DESCRIPTION OF THE INVENTION

By way of example, the present invention is illustrated and described for application in the colon of the lower GI tract of a human patient. However, the present invention is applicable for use in the body lumens of other hollow organs in humans and in other mammals.

Figure 1:
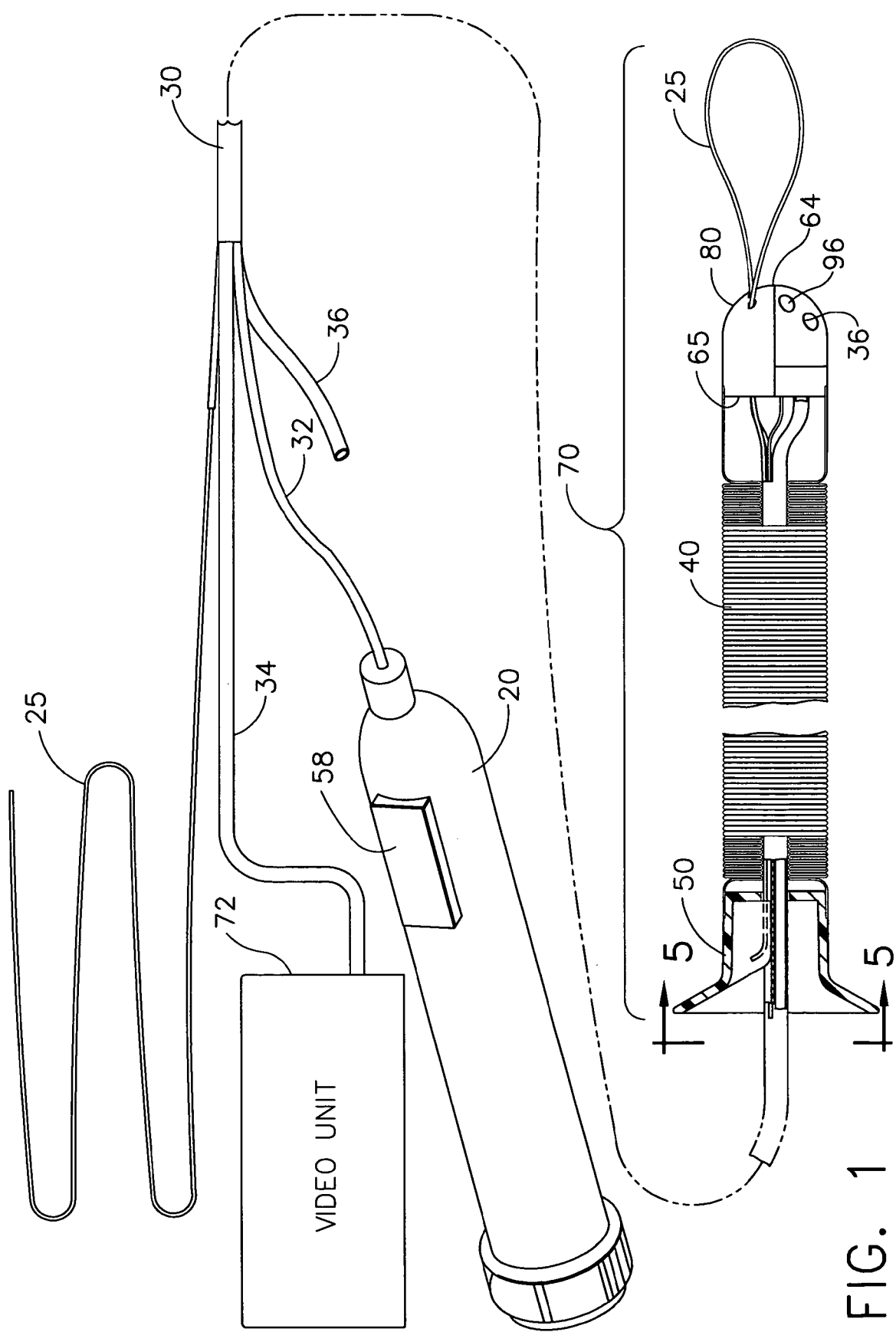
FIG. 1 shows a medical device 70 generally comprising a movable apparatus such as capsule 80 adapted for movement within a body lumen, a compressible sleeve 40, a fixing plate 50, an umbilicus 30, a cable 25, a video unit 72, a handpiece 20, and a motion control 58.

FIG. 1 shows a medical device 70. The medical device 70 can include a movable apparatus, such as a capsule 80 shaped and sized for movement through a body lumen, a compressible sleeve 40, a fixing plate 50, an umbilicus 30, a cable 25, a video unit 72, and a handpiece 20.

Capsule 80 generally has a leading end 64 that is smooth for a traumatic passage through a tortuous path of a gastrointestinal (GI) tract, such as a colon. In one embodiment of capsule 80, leading end 64 is hemispherical and a trailing end 65 is flat to accept the contents contained in umbilicus 30. Other shapes of capsule 80 are possible, such as but not limited to tapered, cylindrical, ovoid, or egg-shaped configurations, to facilitate navigation through the colon.

Compressible sleeve 40 can extend from trailing end 65 of capsule 80 to fixing plate 50. Fixing plate 50 can be anchored to the patient with adhesive. Other methods of attachment to the patient include, but are not limited to glue, tape, or a close-fitting wrap. Suture or staples may also be used, but are less desirable because of the pain involved in their placement or removal. In applications related to the lower GI tract, fixing plate 50 can extend into the patient's anus. A secure attachment of plate 50 to the patients body or other fixture is desirable so that fixing plate 50 provides an anchor, thereby enhancing movement of capsule 80 deeper into the colon.

The proximal portion of umbilicus 30 can extend outside the body and can be connected to equipment, including video unit 72 and handpiece 20. The distal portion of umbilicus 30 can be connected to trailing end 65 of capsule 80 inside the colon. Umbilicus 30 can extend through openings in plate 50 and sleeve 40, and umbilicus 30 can slide through the openings relative to plate 50 and sleeve 40. Umbilicus 30 is preferably made from a lightweight, flexible, plastic, multilumen tube. For example, umbilicus 30 may have four lumens: a 3 mm lumen for a working channel 36, a 3 mm diameter lumen for the wiring assembly 34, a 5 mm diameter lumen to receive a drive cable 32, and a 3 mm lumen to receive cable 25. Many other sizes and combinations of lumens are possible. Umbilicus 30 may also comprise separate thin-wall, flexible plastic tubes that are bundled together with straps, shrink-wrap, or the like.

Cable 25 can provide a track on which capsule 80 is supported and propelled. Cable 25 may be constructed in numerous shapes, including a braided strand of fibers, a coated wire, a flat band, or may have a constant cross sectional shape including circular, triangular, or rectangular. Cable 25 may include a periodic and/or non periodic pattern of features that assist in traction, such as teeth, holes, or grooves. Cable 25 may be made from any suitable material, including without limitation one or more metals including steel, nitinol, aluminum, or titanium, and have diameters including, but not limited to, 0.5 mm to 2.5 mm.

One suitable material for use as a cable 25 is a guidwire having a nitinol core with a diameter of about 0.021 inch to about 0.025 inch surrounded by a stainless steel wire coil having a diameter of about 0.008 inch. The overall diameter can be between about 0.037 inch and about 0.041 inch, and the stainless steel coil may be soldered or otherwise attached at about 50 cm intervals to hold the stainless steel coil in place relative to the nitinol core. Another suitable material for use as a cable 25 is a guidwire marketed as Elite Protector™ Elite 480 wire guide available from Wilson-Cook Medical, Inc. of Winston Salem, N.C., and having a diameter of about 0.035 inch.

A proximal portion of cable 25 extends outside the body, so that an operator can handle it. Cable 25 is fed through umbilicus 30, though capsule 80, to form a cable loop 54 ahead (distally) of capsule 80. As described below, cable loop 54 can be used to navigate around the tortuous path of the colon, eliminating the need for the operator to make constant adjustment of the articulation controls of an endoscope, thus reducing the skill required to intubate the device. As alternatives to cable 25, other suitable track configurations can be used, including without limitation flexible rails, chains, slides, and belts.

Still referring to FIG. 1, video unit 72 supplies power to a lighting device 96 (FIG. 9), and processes video images taken by a visualization device 95 (FIG. 9) in capsule 80 as it moves through the colon so that the operator is able to view the inside surface of the lumen. Lighting device 96 may include a bulb or LED (Light Emitting Diode) contained within capsule 80, or include a fiberoptic, a light pipe, or a lens of a light source contained in video unit 72. One example of a bulb that could be located in capsule 80 is Xenon #724 from Carley Lamps (Torrance, Calif.). Visualization device 95 may be a CMOS (Complementary Metallic Oxide Semiconductor) or CCD (Charged Coupled Device) camera, either of which are commercially available in sizes adaptable to use in capsule 80. For example, a CMOS chip such as #OV7620 from Omnivision Technologies (Sunnyvale, Calif.) could be used. Wiring assembly 34 transfers signals between video unit 72 and lighting device 96 and between video unit 72 and visualization device 95.

Handpiece 20 provides a motion control 58 to activate the propulsion of capsule 80 along cable 25. Capsule 80 can be propelled along cable 25 in any suitable manner. In one embodiment, handpiece 20 contains a motor and operably controls a flexible drive cable 32, which is constructed to transmit torque, to operate a propulsion mechanism 44 (FIG. 7) located inside capsule 80 to move medical device 70 further into the colon. In one embodiment, motion control 58 has a forward and reverse setting to change the rotation of a motor within handpiece 20 so that capsule 80 moves in a forward and backward direction along cable 25.

The proximal portion of working channel 36 extends out of the body to a location near handpiece 20, so that the operator can pass medical instruments in and out of the colon numerous times. The distal portion of working channel 36 extends through capsule 80 to an opening in the outer surface of the leading edge 64 of capsule 80. Medical instruments can be inserted into the proximal end of working channel 36 and be directed through working channel to the opening in the outer surface of the capsule 80 without removing the capsule 80 from the body lumen. Accordingly, the operator can access lumen tissue adjacent the capsule 80 with the medical instruments as the capsule is moved through the lumen. Medical instruments which can be directed through a working channel include without limitation tissue graspers, staplers, cutters, clip appliers, tissue ablation devices, tissue staining devices, and devices for dispensing pharmaceutical agents.

Figure 2:
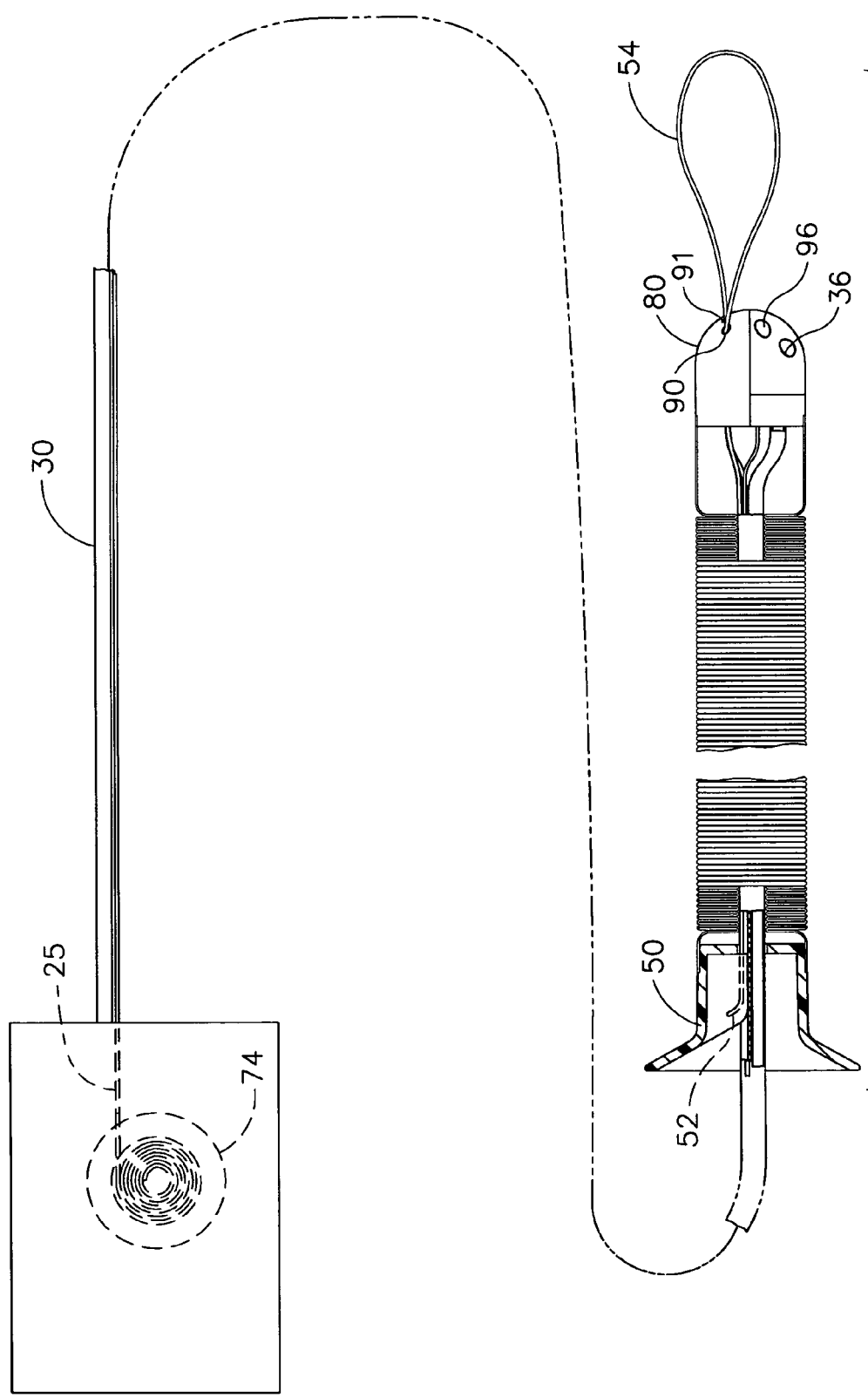
FIG. 2 is a sectional view of medical device 70 shown in FIG. 1 and includes a cable spool 74, a cable anchor 52, and cable 25 formed into a cable loop 54.

FIG. 2 shows medical device 70 of FIG. 1 including a cable spool 74 outside the body, and cable loop 54 ahead (distal) of capsule 80. Cable spool 74 stores a proximal portion of cable 25, and may be used to unwind an additional length of cable 25 through umbilicus 30 and a sliding channel 90, to increase the size of cable loop 54 ahead of capsule 80 in the colon.

Cable loop 54 is formed ahead of capsule 80 from a middle portion of cable 25. One end of cable loop 54 is formed by cable extending distally outward from a sliding channel 90, and the other end (the return end) of cable loop 54 is formed by cable extending proximally into an opening in the outer surface of the capsule 80, where the cable is fed though (and is engaged by) a gripping channel 91 in the capsule 80. The cable extends from the gripping channel 91 proximally through compressible sleeve 40 (outside of umbilicus 30) to cable anchor 52. This arrangement allows an operator to feed an additional portion of cable 25 through sliding channel 90 to increase the size of cable loop 54 (other end of loop is held by gripping channel 91). As cable loop 54 increases in size, it "unfurls" inside the lumen directly ahead of capsule 80, and generally conforms to bends or curves in the lumen, thereby laying a track along and/or distal to the bend on which to propel the capsule. This arrangement of cable loop 54 can be advantageous in simplifying the process of navigating the colon. The operator can simply add length to the loop portion of the cable to negotiate bends and turns in the GI tract, rather than trying to manipulate the end of a guide tube or guide wire through the three dimensional curvature of the lumen. The operator then uses motion control 58 (FIG. 1) to advance capsule 80 in a forward direction along the track (the cable loop 54) to move the capsule 80 through the bend in colon.

Figure 3:
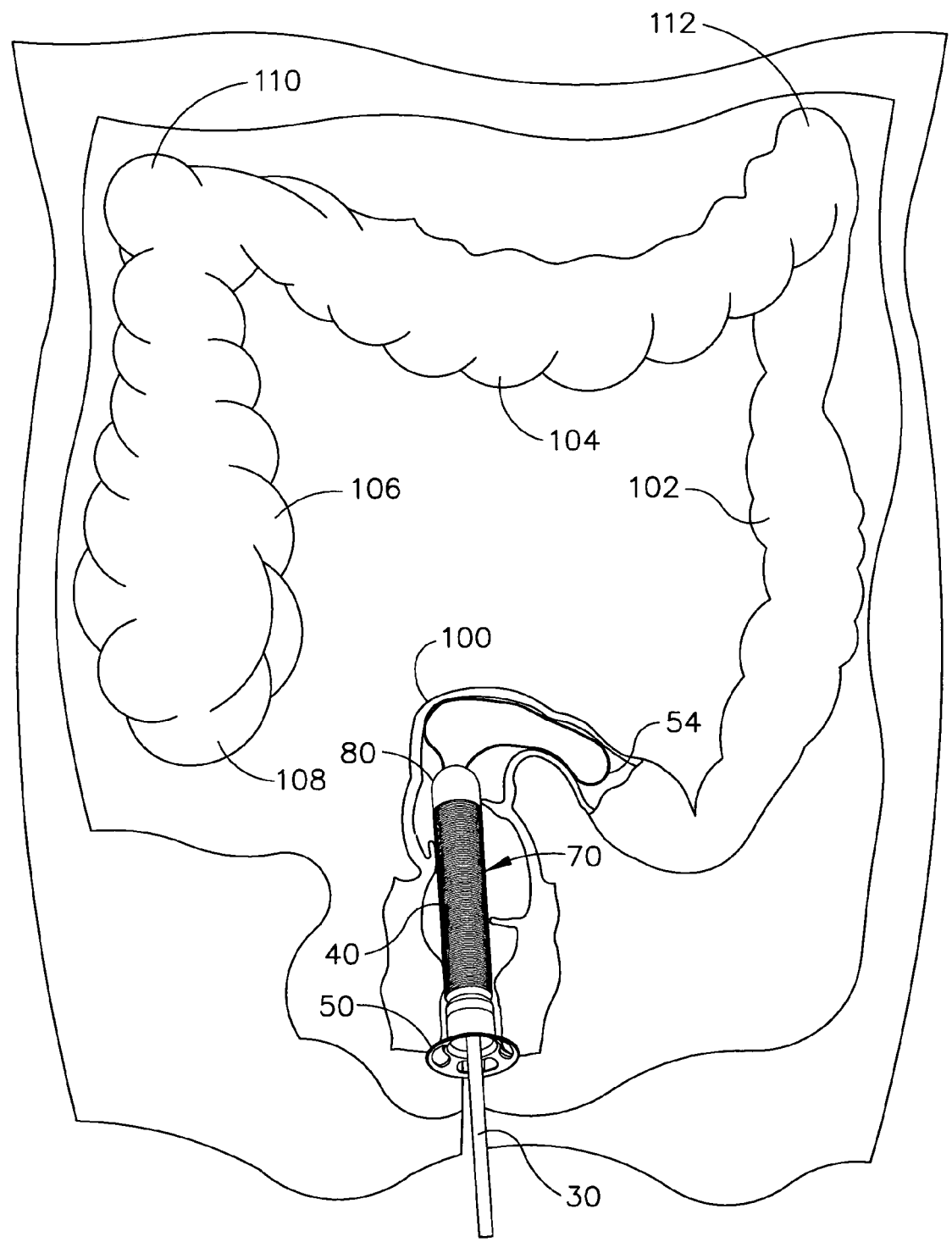
FIG. 3 is a cross sectional view of a portion of the gastrointestinal tract with medical device 70 placed relative to anatomical milestones including a sigmoid 100, a descending colon 102, a left splenic flexure 112, a transverse colon 104, a hepatic flexure 110, an ascending colon 106, and a cecum 108.

FIG. 3 shows medical device 70 positioned in the colon. Cable loop 54 is introduced first, with capsule 80, compressible sleeve 40, and fixing plate 50 trailing behind it. Fixing plate 50 can then be securely affixed to the anus or other suitable location with adhesive or by other means, creating an anchor point relative to the patient.

Figure 9:
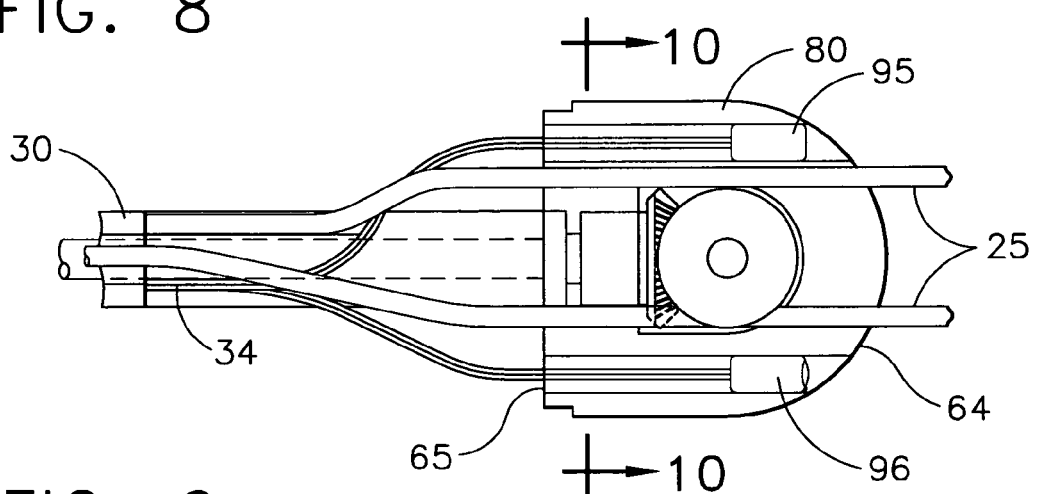
FIG. 9 is a cross-sectional view of capsule 80 taken at line 9-9 of FIG. 8, showing wiring assembly 34, a lighting device 96, and a visualization device 95.

Cable loop 54 is shown deployed around a bend in the sigmoid colon 100. The operator monitors progress of capsule 80 and cable loop 54 by viewing video unit 72 (FIG. 1), which displays images taken by visualization device 95 (FIG. 9). When cable loop 54 reaches a sufficient orientation to navigate a bend in the colon, capsule 80 is propelled a short distance along cable 25 by propulsion mechanism 44 (FIG. 7) under control of the operator who activates motion control 58 (FIG. 1). This process shortens the length of cable loop 54 ahead (distal) of capsule 80.

To further advance capsule 80 deeper into the colon, the operator slides more of the proximal portion of cable 25 through umbilicus 30 and sliding channel 90 to again increase the size of cable loop 54 ahead of capsule 80. This procedure lays additional track through additional bends that are deeper in the colon, such as the left splenic flexure 112 or the hepatic flexure 110. The operator continues to slide cable 25 and activate motion control 58 (FIG. 1), in sequence, to incrementally move capsule 80 through the descending colon 102, transverse colon 104, and ascending colon 106 to cecum 108.

As capsule 80 advances along cable 25, compressible sleeve 40 begins to uncompress (increase in length) so that a smooth, uninterrupted surface is maintained from fixing plate 50 to capsule 80.

Figure 4:
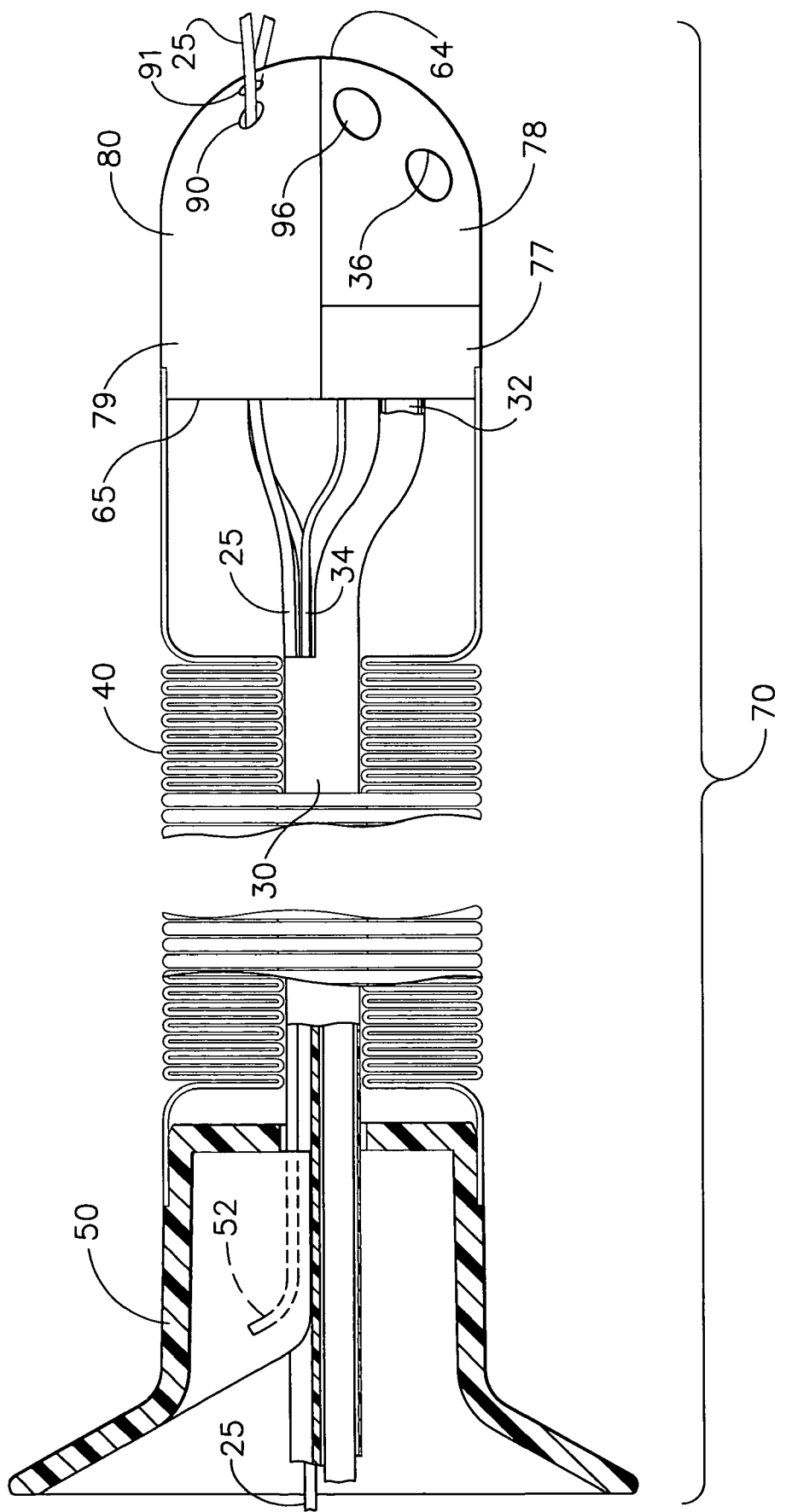
FIG. 4 is a detailed view of medical device 70 of FIG. 1 showing a wiring assembly 34, a drive cable 32 and capsule 80 comprising a leading end 64, a trailing end 65, 1st section 77, a 2nd section 78, and a 3rd section 79.
Figure 7:
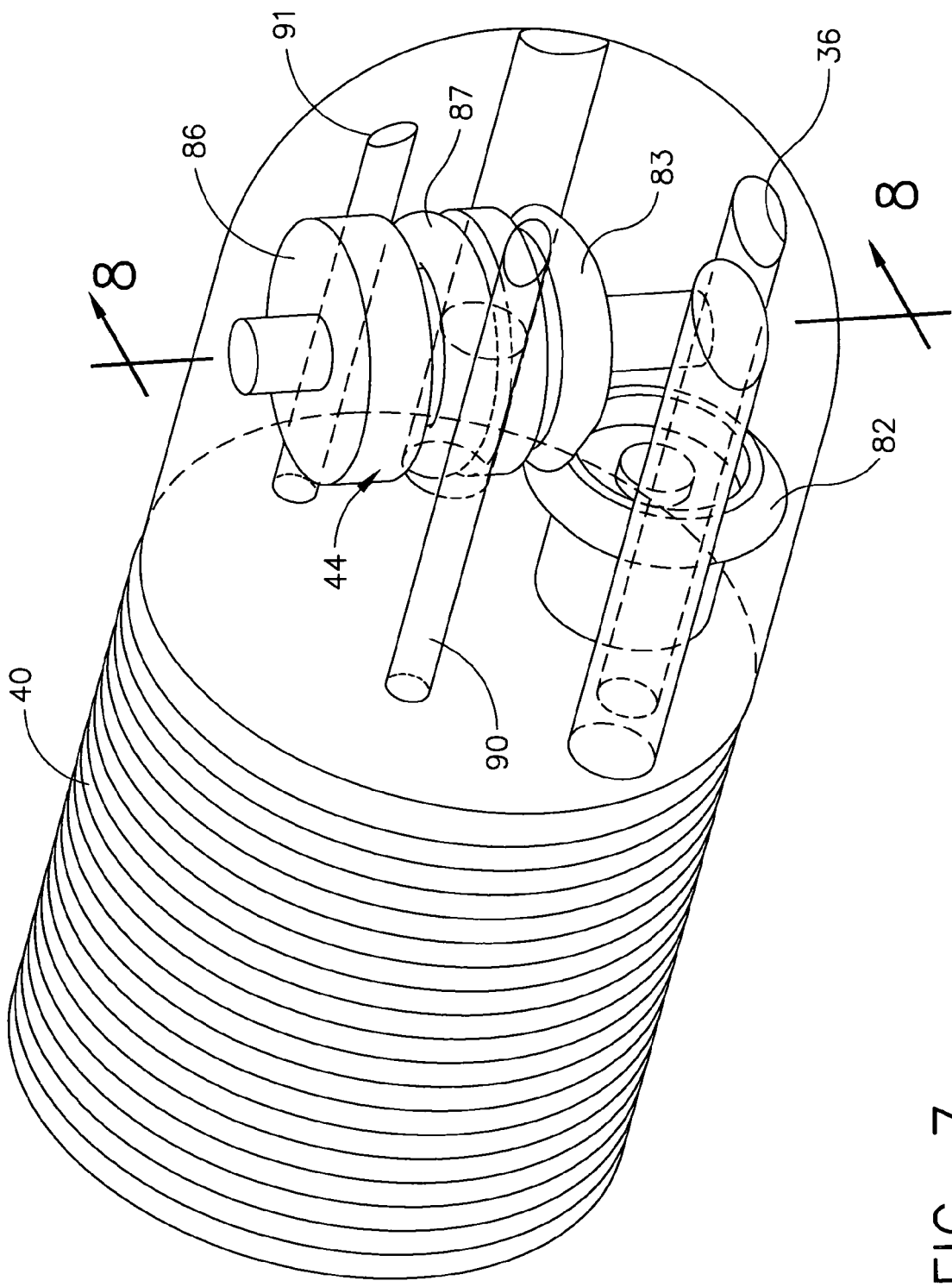
FIG. 7 is an isometric view of capsule 80 of FIG. 4, showing a sliding channel 90, a gripping channel 91, working channel 36, and a propulsion mechanism 44 comprising a first miter gear 82, a second miter gear 83, a pulley 86, and a pulley grip 87.

FIG. 4 is a detailed view of medical device 70 generally comprising capsule 80, compressible sleeve 40, fixing plate 50, and umbilicus 30. In this embodiment, capsule 80 is comprised of three sections (a 1st section 77, a $2^{nd}$ section 78, and a $3^{rd}$ section 79) for assembly and contains propulsion mechanism 44 (FIG. 7). Other embodiments with a different arrangement or number of sections, or other locations of propulsion mechanism 44 are possible. Visualization device 95 (FIG. 9) and lighting device 96 (FIG. 9), located near leading end 64 of capsule 80, communicate with video unit 72 through wiring assembly 34 to allow visualization of the inside of the lumen in the vicinity of capsule 80. Working channel 36 allows an operator to repeatedly pass medical instruments in and out of the patient to perform treatment in the vicinity of capsule 80, without removing capsule 80 from the body lumen.

Compressible sleeve 40 can perform at least two functions. First, compressible sleeve can provide a smooth, uninterrupted, flexible connection between fixing plate 50 and capsule 80 as it advances deeper into the colon, to thereby assist in protecting the body lumen from damage as medical device 70 navigates the colon. Additionally, compressible sleeve 40 can act to radially confine a portion of cable 25 located between gripping channel 91 and cable anchor 52 to assist in the propulsion of capsule 80 in a forward direction deeper into the colon. By radially confining a portion of cable 25 between gripping channel 91 and anchor 52, the sleeve 40 can assist in preventing a secondary loop from forming in cable 25 between capsule 80 and fixing plate 50 (prevents formation of a cable loop behind (proximal) of capsule 80). Compressible sleeve 40 may be made from any suitable material, including without limitation ePTFE (expanded polytetrafluoroethylene), or other suitable flexible material that stretch or otherwise increase in length to accommodate the increased distance between the anchor 52 and the capsule 80 as the capsule moves deeper into the GI tract.

Propulsion mechanism 44 uses a portion of cable 25 inside gripping channel 91 to propel capsule 80 further into the colon. As motion control 58 (FIG. 1) is activated, propulsion mechanism 44 moves a portion of cable 25, initially comprising cable loop 54, back through gripping channel 91 to a position between capsule 80 and fixing plate 50. Therefore, the length of cable 25 between capsule 80 and fixing plate 50 increases. Because cable 25 is anchored to the patient by fixing plate 50 and radially confined by compressible sleeve 40, cable 25 supplies an axial force to counteract a traction force applied by propulsion mechanism 44, resulting in capsule 80 being propelled further into the colon.

The location of propulsion mechanism 44 inside capsule 80 is advantageous because it locally propels capsule 80 a short distance from a position already within the colon. This decreases the forces needed to push an entire length of endoscope or other long flexible extension through the tortuous colon. However, other mechanisms or locations for mechanisms may be used to accomplish the propulsion. For example, propulsion mechanism 44 can be positioned anywhere that allows the length of cable 25 between fixing plate 50 and capsule 80 to vary in length, including a separate pod between capsule 80 and fixing plate 50, a separate housing attached to fixing plate 50, or contained within a portion of fixing plate 50.

Figures 5, 6:
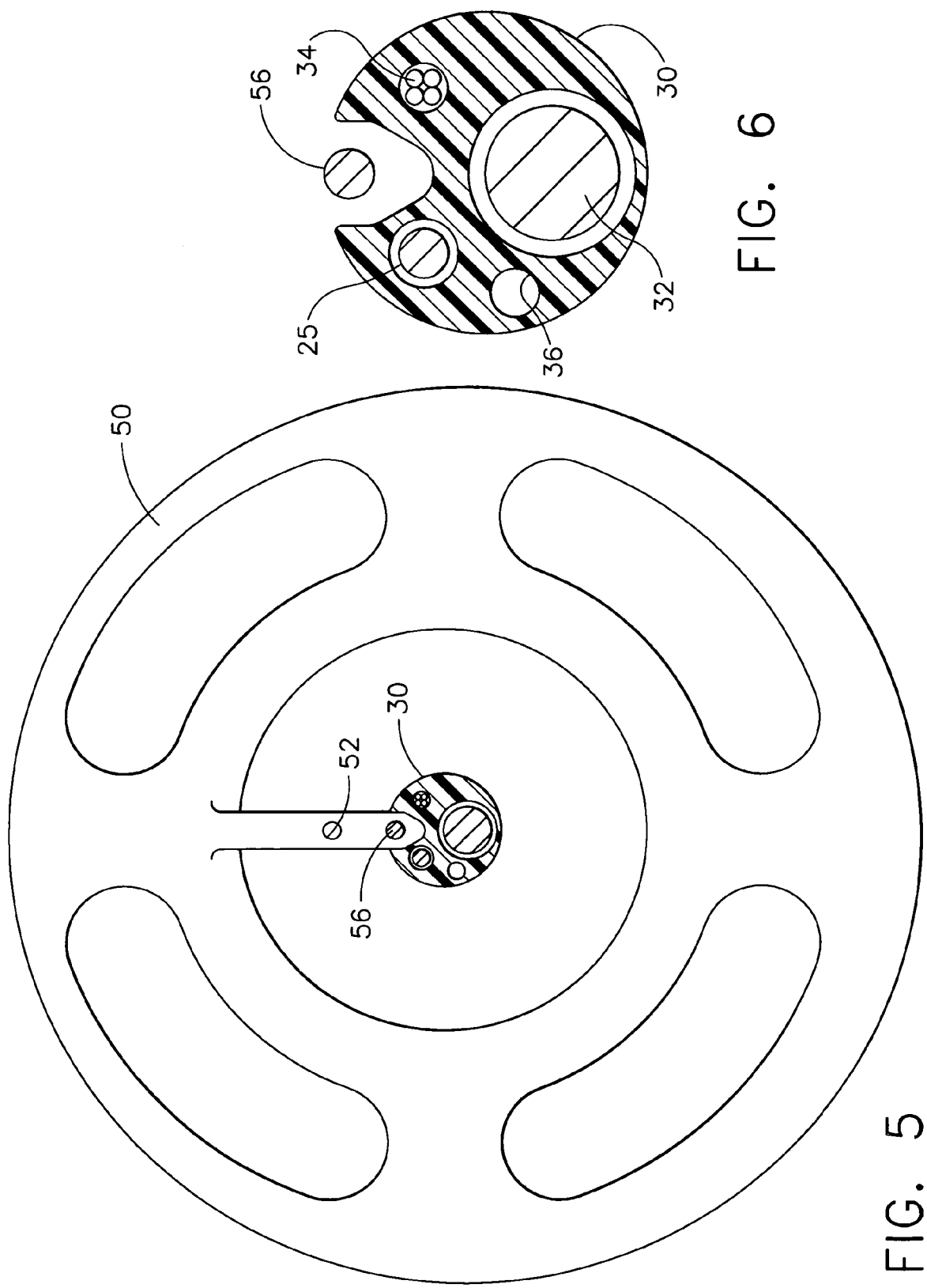
FIG. 5 is a cross-sectional view taken at line 5-5 of FIG. 1, showing fixing plate 50, cable anchor 52, a centering attachment 56, and umbilicus 30.
FIG. 6 is a detail view of a cross-section of umbilicus 30 from FIG. 5, showing cable 25, wiring assembly 34, drive cable 32, and a working channel 36.

FIG. 5 is a cross section of medical device 70 taken at line 5-5 of FIG. 1, showing one embodiment of fixing plate 50 having a relatively large diameter sized for securing it to a patient's anus. Cable anchor 52 is shown as a rigid attachment to fixing plate 50, so that the distal portion of cable 25 does not move relative to fixing plate 50. Centering attachment 56 holds umbilicus 30 in the center of fixing plate 50 for alignment through the anus into the colon.

FIG. 6 shows a detailed view of the cross section of umbilicus 30 from FIG. 5, including a lumen for cable 25, a lumen for wiring assembly 34, a lumen for drive cable 32, and working channel 36. FIG. 6 indicates the relative positions and sizes of these lumens and elements in this embodiment of umbilicus 30. Numerous other sizes and arrangements are possible. For example, additional working channels could be added, working channel 36 could be sized larger to allow for passage of larger instruments, or the lumen for drive cable 32 could be smaller. In general, it is advantageous to have a small diameter and lightweight umbilicus 30 so that capsule 80 has as little drag as possible when advancing through the colon.

FIG. 7 is an isometric view of one embodiment of compressible sleeve 40 and capsule 80 including sliding channel 90, gripping channel 91, working channel 36, and propulsion mechanism 44 including a first miter gear 82, a second miter gear 83, a pulley 86, and a pulley grip 87. This illustration shows the relative positions of these elements in three-dimensional space.

Figure 8:
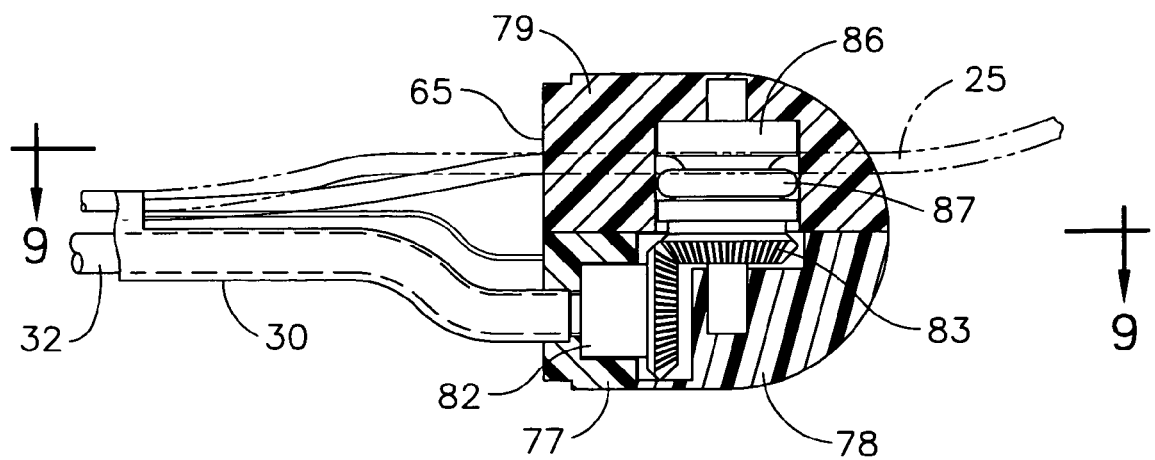
FIG. 8 is a cross-sectional view of capsule 80 taken at line 8-8 of FIG. 7, showing drive cable 32, first miter gear 82, second miter gear 83, pulley 86, pulley grip 87, and cable 25.

Propulsion mechanism 44 works by changing the length of cable 25 between capsule 80 and fixing plate 50, which has been secured to the patient's body. In this manner, capsule 80 can move deeper into the colon when this length of cable 25 increases, and moves backward out of the colon when this length decreases. In this embodiment, propulsion mechanism 44 comprises a gear system described below contained within capsule 80, but other locations and systems are possible FIG. 8 is a cross sectional view of capsule 80 taken at line 8-8 of FIG. 7, showing an arrangement of gears in this embodiment of propulsion mechanism 44 (FIG. 7). The distal portion of drive cable 32 passes through trailing end 65 of capsule 80 and coaxially connects to first miter gear 82. Drive cable 32 is constructed to transmit torque from handpiece 20 to first miter gear 82, so that when the operator activates motion control 58 (FIG. 1), first miter gear 82 rotates around an axis collinear with drive cable 32.

In the embodiment shown, miter gears 82 and 83 are supported in the capsule 80 (such as by a suitable bearing or bushing) for rotation about their respective axes of rotation, which are generally perpendicular to one another. The teeth of first miter gear 82 and second miter gear 83 are each cut at a 45-degree angle, so that rotational motion around the axis of drive cable 32 is converted to rotation around another axis 90 degrees to the first. Therefore, when the operator activates motion control 58, first miter gear 82 rotates about its axis of rotation, and transmits torque to second miter gear 83, causing gear 83 to rotate about its axis of rotation.

Pulley 86 is coaxially coupled to second miter gear 83, and pully 86 is supported for rotation about the axis of rotation of miter gear 83. When second miter gear 83 rotates, pulley 86 rotates with gear 83 around its axis of rotation. A portion of cable 25 contained within gripping channel 91 is in contact with pulley 86. Gripping channel 91 and pulley grip 87 act in concert to prevent slippage and apply a traction force from pulley 86 to cable 25, as pulley 86 rotates. In a fashion similar to a train wheel propelling a locomotive along a railroad track, pulley 86 propels capsule 80 along cable 25. The result of this motion increases the length of cable 25 between capsule 80 and fixing plate 50 to propel capsule 80 further into the colon.

FIG. 9 is a sectional view of capsule 80 taken at line 9-9 of FIG. 8. It shows the relative positions of visualization device 95, lighting device 96, cable 25, and pulley 86 within capsule 80. In this embodiment, wiring assembly 34 divides into two bundles before it passes through trailing end 65 of capsule 80. One bundle communicates with lighting device 96, and the other bundle communicates with visualization device 95. Lighting device 96 shines light to illuminate the region of the lumen in the vicinity of capsule 80. Visualization device 95 transmits images taken at this location back through wiring assembly 34 to video unit 72 for the operator to view.

Figure 10:
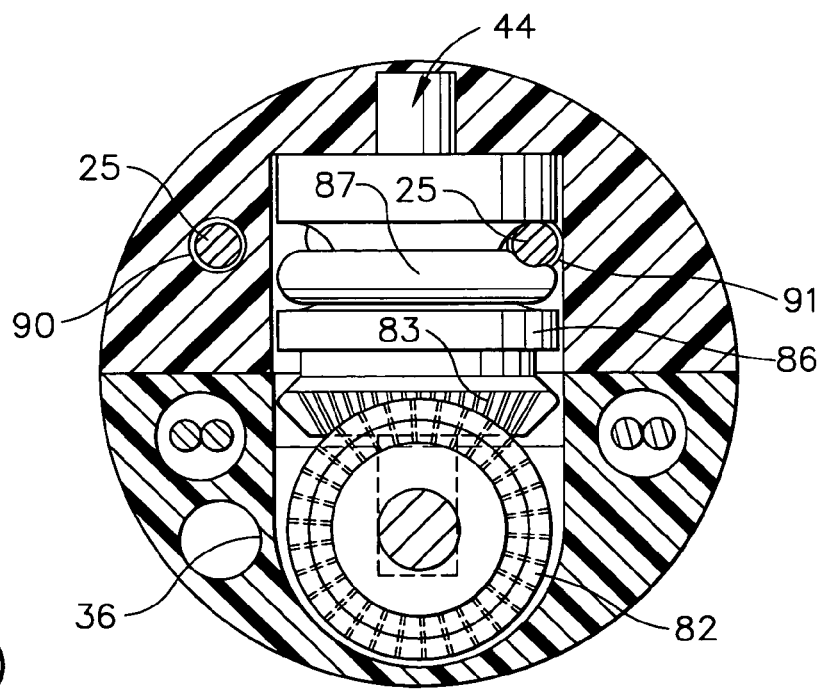
FIG. 10 is a cross-sectional view of capsule 80 taken at line 10-10 of FIG. 9, showing first miter gear 82, second miter gear 83, pulley 86, pulley grip 87, cable 25 within sliding channel 90, and cable 25 within gripping channel 91.

FIG. 10 is a cross sectional view of capsule 80 taken at line 10-10 of FIG. 9. As shown in this view gripping channel 91 is positioned and aligned so as to direct cable 25 into the pulley grip 86, and pulley grip 86 holds cable 25 in contact with pulley 86. Sliding channel 90 is also shown in a position within the GI tract which is free of obstructions (e.g. sharp curves or bends in the colon) so that the operator can slide cable 25 in a forward direction to increase the size of cable loop 54 (FIG. 2) ahead of capsule 80. This embodiment shows wiring assembly 34 split into two bundles, one bundle on either side of first miter gear 82. One of the bundles connects to visualization device 95, and the other bundle connects to illuminating device 96.

Generally, medical device 70 is propelled through the colon under control of the operator for examination and treatment of sites within the lumen. Medical device 70 is placed into a patient's colon through the anus. Fixing plate 50 is affixed to the patient at this location. The operator advances a proximal portion of cable 25 through umbilicus 30 and sliding channel 90 to increase the size of cable loop 54 ahead of capsule 80. As described above, this process provides a path around the tortuous bends of the colon for capsule 80 to follow.

While viewing video unit 72, the operator sees the inside of the lumen in the vicinity of capsule 80. Motion control 58 of handpiece 20 is activated to advance capsule 80 along cable 25, moving it deeper into the colon. To further advance capsule 80, the operator again feeds cable 25 to further increase the size of cable loop 54, and again activates motion control 58. These steps are repeated until capsule 80 reaches a depth deemed sufficient by an operator, which is cecum 108 in many cases. At any time during the procedure, the operator may introduce and remove medical instruments through working channel 36 to treat a site in the patient. Medical device 70 is therefore useful for diagnosis as well as therapy.

Figure 11:
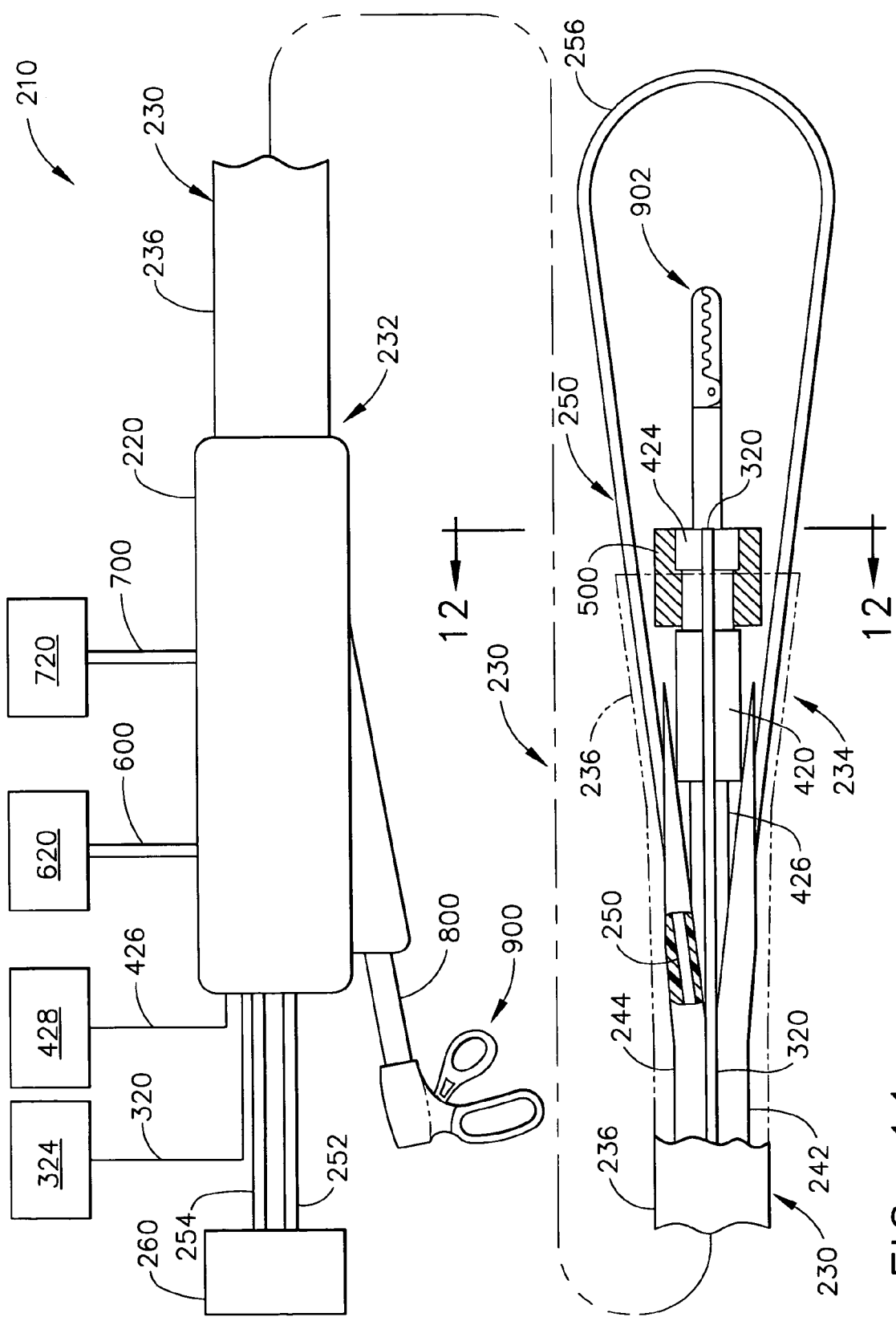
FIG. 11 is a schematic illustration of a medical device according to one embodiment of the present invention, showing a flexible, elongate member extending from a hand piece of the device, and a loop track extending from the distal end of the elongate member.

FIG. 11 illustrates a medical device 210 according to another embodiment of the present invention. Medical device 210 includes an elongate, flexible member 230 extending distally from a handpiece 220. Flexible member 230 can be attached, directly or indirectly, to handpiece 220, and can be in the form of an umbilicus. By "flexible" it is meant that the member 230 has sufficient bending flexibility to allow the member 230 to be inserted into and advanced along a body lumen, such as the GI tract, without trauma to the patient. Member 230 is elongate in the sense that it has a length sufficient to permit a proximal end 232 of the member 230 associated with handpiece 220 to be positioned outside the body, or near the entrance to the body lumen, while a distal end 234 of the member 230 is advanced into the body lumen. In one embodiment, the flexible member 230 can have a length of at least about 36 inches, and more particularly for use in the colon, a length of at least about 100 inches. Flexible member 230 can have an outer diameter of between about 0.1 and about 1.0 inches to be positionable and advancable within the GI tract. In one embodiment, flexible member 230 can be in the form of a catheter, or have a catheter-like configuration, and can have an outer diameter of between about 4-6 mm, more particularly about 5 mm.

Flexible member 230 can include an outer sheath 236 which extends along substantially the full length of flexible member 230. A suitable sheath can be made of a thin, flexible polymeric film or other suitable flexible material. One suitable sheath material is porous teflon tubing (PTFE) having a thickness of about 0.02 inches. A suitable material is manufactured by International Polymer Engineering of Tempe Ariz.

In FIG. 11, a portion of the sheath 236 at the distal end 234 of the flexible member 230 is shown in phantom to reveal internal features of the flexible member 230 and components associated with the distal end 234 of flexible member 230. Flexible member 230 includes a track guide for receiving a track 250 upon which the flexible member 230 can be advanced. In FIG. 11 the track guide is shown in the form of two track guide tubes 242 and 244. Track 250 is received in track guide tubes 242 and 244, and can slide within tubes 242 and 244. Track guide tubes are disposed within the sheath 236, and can extend from proximal guide tube ends associated with the handpiece 220 to distal ends associated with the distal end of flexible member 230. In FIG. 11, the distal ends of the track guide tubes are shown cut at a bevel angle to accommodate the track 250 extending from the flexible member 230 at an angle with respect to the longitudinal axis of the flexible member 230.

Track guide tubes 242 and 244 can be joined, directly or indirectly, in any suitable manner (e.g. with adhesive, elastic bands, ultrasonic bonding) to the sheath 236 and/or to handpiece 220 so that the tubes 242, 244, the sheath 236, and the handpiece 220 move together. Track guide tubes 242 and 244 can also fit tightly in sheath 236 and can be fixed to sheath 236 at either end by heat shrink tubing (not shown).

Figure 12:
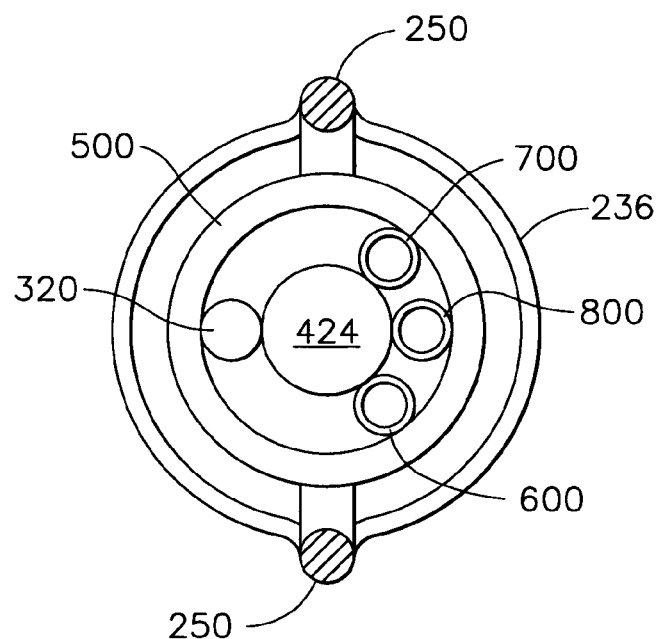
FIG. 12 is a cross-sectional schematic illustration taken along section 12-12 in FIG. 11 and showing the distal end of the flexible elongate member.

A visualization device and a light source can also be associated with the distal end of the flexible member 230. In FIG. 11 and FIG. 12, an optical fiber 320 extends from a light source 324, through handpiece 220 and through flexible member 230 to terminate at the distal end of flexible member 230. Optical fiber 320 carries light from light source 324 to illuminate lumen tissue adjacent the distal end of flexible member 230. A camera 420 and associated camera optics 424 can be disposed at the distal end of the flexible member 230. A camera can include built in optics and electronics, and can include CCD or CMOS capability. A suitable camera is an MVC-Snake-1 camera manufactured by Micro Video Products having a self contained CCD camera with built in optics and electronics. Alternatively, a CMOS camera such as one manufactured by Welch Allyn of Schenectady N.Y. could be used. Signal cable 426 extends proximally from camera 420 through flexible member 230 and handpiece 220 to provide a signal to a monitor 428 or other suitable receiver/recorder.

Flexible member 230 can also include various channels/passageways for conveying gases, liquids, or working devices from a point outside the patient to the tissue adjacent the distal end 234 of flexible member 230. Referring to FIGS. 11 and 12, a vacuum tube 600 can extend through flexible member 230 and handpiece 220 to be in communication with a vacuum source 620 for providing vacuum to the distal end of flexible member 230. Likewise, a fluid tube 700 can extend through member 230 and handpiece 220 to a supply 720 of fluid (e.g water, saline solution, lubricating fluids). FIG. 12 also shows the opening of a working channel tube 800 at the distal end of flexible member 230. Working channel tube 800 can extend through member 230 and handpiece 800 to receive a medical instrument 900. For instance, once the distal end of flexible member 230 is positioned at a desired location in the body lumen, a medical instrument 900, such as one having a forceps end 902 as shown in FIG. 11, can be introduced through channel tube 800 to access tissue adjacent the distal end of flexible member 230. In FIGS. 11 and 12, a band 500 is shown holding the optical fiber 320 and tubes 600, 700, and 800 against camera 420.

Track 250 can extend the length of flexible member 230. In FIG. 11, Track 250 is shown to include first and second ends 252 and 254, and a loop portion 256 disposed along the track intermediate the first and second ends 252 and 254. Loop portion 256 is disposed distally of the distal end of flexible member 230. First and second ends 252 and 254 can extend proximally from the handpiece 220. If desired, the ends of the track extending proximally from the handpiece 220 can be wound, coiled, or otherwise supported on a suitable spool or receiver to prevent tangling of the ends 252 and 254. The track 250 extends in a generally continuous manner distally of the flexible member 230 (there are no track ends in the lumen distal of the flexible member 230).

Figure 14:
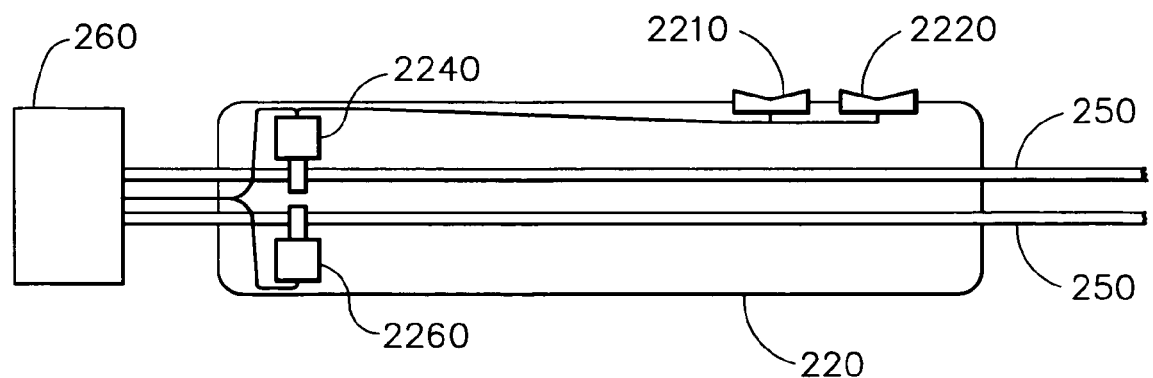
FIG. 14 provides a schematic illustration of a handpiece having motors for advancing and retracting a track.

First and second ends can be manually manipulated by an operator's hands to advance either end 252 or 254 toward handpiece 220 to advance the track 250 through flexible member 230, to thereby enlarge the loop portion 256. Alternatively, the ends 252 and 254 can be associated with a control unit 260 as shown schematically in FIG. 11. In an embodiment shown in FIG. 14, handpiece 220 can include two switches 2210 and 2220 for independently controlling reversible motors 2240 and 2260, which can be mounted within handpiece 220. The motor speed and/or torque can be controlled by control unit 260, and the motors can include a coupling mechanism which applies frictional force to the track 250 to drive the track ends forward (distally toward flexible member 230) or backward (proximally away from flexible member 230) depending on the position of switches.

In the embodiments shown, track 250 is a single piece which extends from first end 252, passes through handpiece 220 and extends distally through guide tube 242 to exit guide tube 242 near the distal end 234 of flexible member 230. Track 250 extends from the bevel cut distal end of guide tube 242 to extend around loop portion 256 and enters the bevel cut distal end of guide tube 244 on substantially the opposite side of flexible member 230 from which track 250 exits guide tube 242. The loop portion 256 comprises a smooth, rounded arc or other curve in which the track 250 turns through (subtends) an angle of at least about 90 degrees, more particularly at least about 180 degrees. In FIG. 11 of the drawings, the track 250 turns through an angle of more than 180 degrees in loop portion 256. Track 250 extends proximally through guide tube 244 and back through handpiece 220 to second end 252. In FIG. 11, a portion of guide tube 244 is shown cut away to illustrate track 250 extending through the guide tube 244.

In order to advance the flexible member 230 (and its associated components) into the body lumen, the distal end of the flexible member 230 can be positioned in the entrance of the lumen. One (or both) track ends 252 and 254 can be advanced toward handpiece 220 (e.g. by pushing gently on the track ends), while the handpiece 220 and flexible member 230 are held stationary. Advancing either end of the track 250 causes the loop portion 256 to increase in length and the track to "unfurl" as it advances out of the confines of the distal end of flexible member to advance within the lumen while following the curvature of the lumen. Once the loop portion 256 has been advanced distally from the flexible member 230 (as can be viewed with camera 420), the flexible member 230 can be advanced distally along the track 250. Flexible member 230 (and associated camera 420 and optical fiber 320) are advanced further into the body lumen by pushing distally on the handpiece 220, and simultaneously pulling proximally on either track end 252 or track end 254. Without being limited by theory, it is believed that by pushing the handpiece 220 and attached flexible member 230, while at the same time pulling back (proximally) on one of the track ends 252 and 254, the force required to advance flexible member 230 through the lumen (e.g. GI tract) is reduced. In particular, in one embodiment, the handpiece 220 can be pushed distally while pulling back on one, but not both, ends 252/254.

Figure 13A:
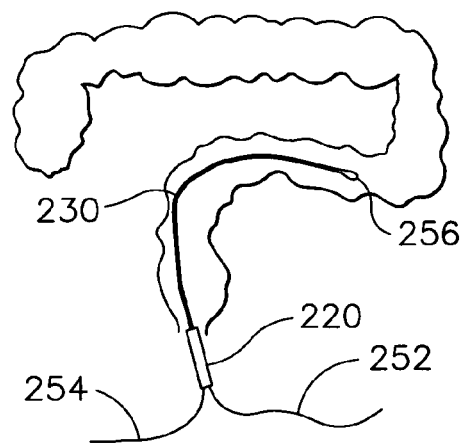
FIGS. 13A-E illustrate advancing the medical device shown in FIG. 11 through a portion of the colon.
Figure 13B:
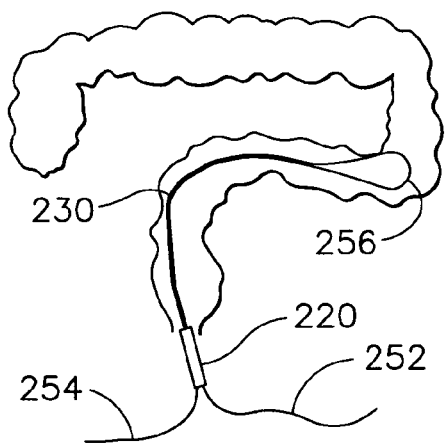
Figure 13C:
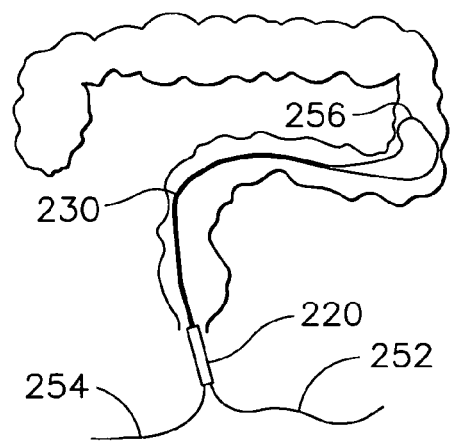
Figure 13D:
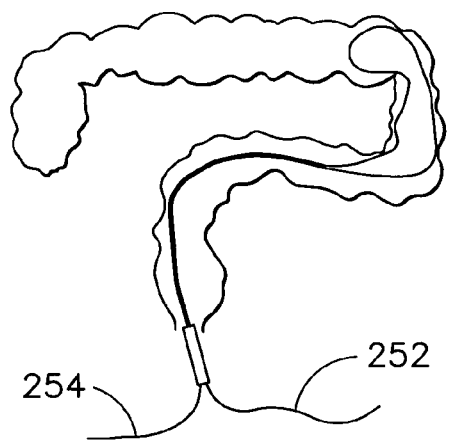
Figure 13E:
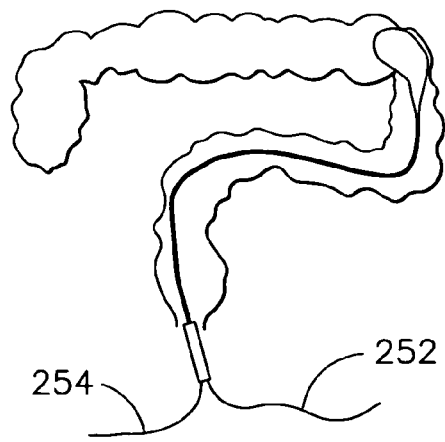

FIGS. 13A-E illustrate schematically how the track 250 can be advanced in the colon, and how the flexible member 230 can then be advanced along the track to position the distal end of the flexible member 230 at a desired location in the colon. In FIG. 13A, the track 250 is shown in a relatively retracted configuration after initial insertion of the medical device into the GI tract. In FIGS. 13B-13D, the track is advanced distally through the flexible member 230 (by pushing one or both the ends 252 and 254 toward handpiece 220). Advancing track 250 through handpiece 220 and member 230 enlarges loop portion 256, and unfurls loop portion 256. In FIG. 13D the loop 256 is shown unfurled to a position associated with the beginning of the transverse colon. The flexible member 230 and associated camera and light source can then be advanced to the transverse colon, as shown in FIG. 13E, by pushing the handpiece/flexible member 230 distally into the GI tract, while simultaneously pulling back (proximally) on one of the ends 252 and 254 of the track 250. In FIG. 13E the loop portion 256 has retracted proximally in the colon relative to its position in FIG. 13D as a result of pulling back on one of the ends 252/254. The steps shown in sequence in FIGS. 13B-E can be repeated, as desired, to position the distal end of the flexible member 230 at a desired location.

Track 250 can be a guide wire having a generally round cross section. One suitable material for use as track 250 is a guidwire having a nitinol core with a diameter of about 0.021 inch to about 0.025 inch surrounded by a stainless steel wire coil having a diameter of about 0.008 inch. The overall diameter can be between about 0.037 inch and about 0.041 inch, and the stainless steel coil may be soldered or otherwise attached at about 50 cm intervals to hold the stainless steel coil in place relative to the nitinol core. Another suitable material for use as a track 250 is a guidwire marketed as Elite Protector™ Elite 480 wire guide available from Wilson-Cook Medical, Inc. of Winston Salem, N.C., and having a diameter of about 0.035 inch. The track can have length of about 15 feet or more, depending on the length of lumen being investigated Track 250 slides within track guide tubes 242 and 244. Track guide tubes 242 and 244 can be formed of a low friction material, or be treated to have a low friction coating. In one embodiment, tubes 242 and 244 can be reinforced Teflon tubing to provide low friction interface with track 250. The tubing can be a wire re-inforced Teflon tube, such as is manufactured by International Polymer Engineering of Tempe Ariz. The outer diameter can be less than or equal to about 0.10" and the wall thickness can be about 0.016".

While the track guide in FIG. 11 is shown as a tube, it will be understood that other guide geometries can be employed, including without limitation channels, rails, and grooved surfaces, as guides for supporting and guiding track 250. In yet another embodiment, the interior diameter of the sheath 236 can be adapted to provide a track guide.

While two guide tubes are illustrated in FIG. 11, in an alternative embodiment, a single guide tube could be used (e.g. guide tube 242), and the track 250 could extend from a first end (located outside the patient) through handpiece 220 and guide tube 242, extend around loop portion 256, and then re-enter guide tube 242. Alternatively, the track 250 could extend from a first end located outside the patient, through the handpiece 220 and guide tube 242, extend around the loop portion 256, and have a second end fixed at or near the distal end of the flexible member 230 (in which case a single track end would extend outside the patient, and this track end would be advanced toward handpiece 220 to increase loop portion 256).

The camera and light source located at the distal end of flexible member 230 can be built into the flexible member 230, so as not to be removed. Alternatively, the camera and light source could be a sealed assembly which is releasably attached to the flexible member 230 (such as by threaded attachment, snap ring attachment, bayonet style attachment, and the like). In one embodiment, the flexible member 230 (with associated guide tubes, fluid tubes, and working channel) can be disposable, and the camera and optics can be reusable.

Figure 16:
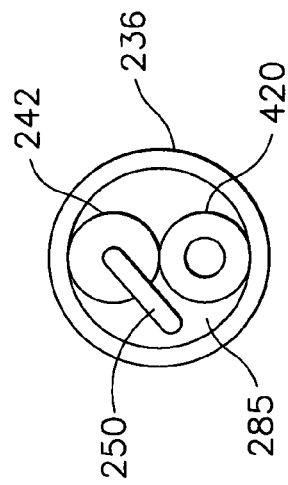
FIG. 16 is an end view taken along section 16-16 in FIG. 15.
Figure 15:
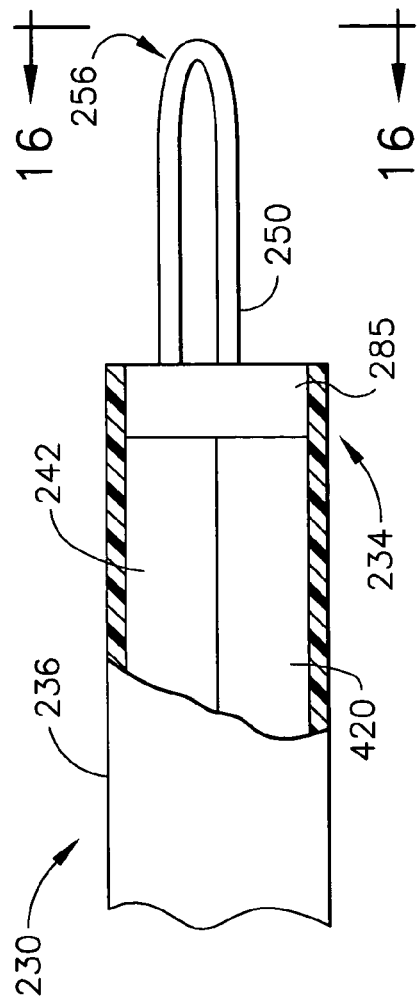
FIG. 15 provides a schematic illustration of an embodiment having a single guide tube and having an end of the track fixed at or near the distal end of the flexible member.

FIG. 15 and FIG. 16 (an end view taken at section 15-15) illustrate an embodiment having a single guide tube 242, along with a camera unit and light source in self contained unit 420. In FIG. 15, a portion of sheath 236 is shown cut away. The track 250 extends from guide tube 242, turns through loop portion 256, and is attached at the distal end of flexible member 230, such as by being fixed to an end piece 285 positioned at the distal end of flexible member 230.

Figure 18:
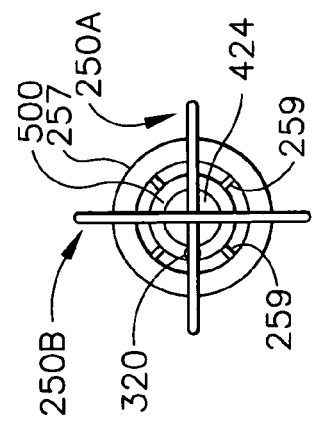
FIG. 18 is an end view taken along section 18-18 in FIG. 17.
Figure 17:
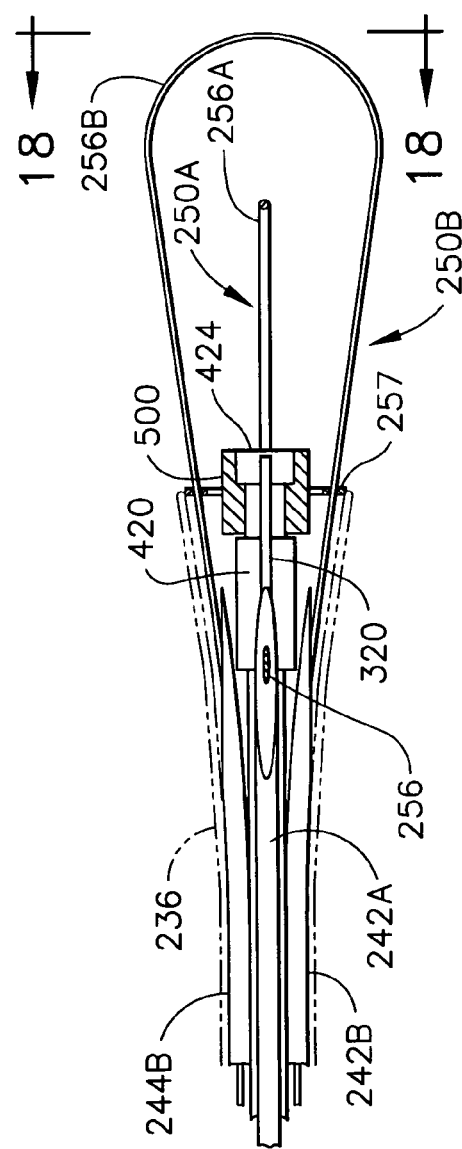
FIG. 17 is a schematic illustration of an embodiment including two sets of guidewires and two track loop portions which can be supported in generally perpendicular planes.

FIGS. 17 and 18 illustrate an embodiment comprising two tracks 250A and 250B, and corresponding track loop portions 256A and 256B which are disposed in generally perpendicular planes. In FIG. 17, the sheath 236 is shown in phantom to reveal guide tracks 242A, 242B, and 244B (guide track 244A not visible), as well as optical fiber 320 and camera unit 420. In the embodiment shown in FIGS. 17 and 18, optical fiber 320 can pass through an aperture hole in a band 500, and band 500 can hold optical fiber 320 adjacent camera 420. Other tubes passageways (e.g. 600, 700, 800 not shown in FIGS. 17 and 18) can also be supported in apertures in band 500. Track retainer ring 257 is provided to hold and/or space tracks 250A and 250B in a desired position. Track retainer ring 257 can include apertures spaced circumferentially at 90 degree intervals around ring 257 (apertures not shown) through which tracks 250A and 250B can slide. Accordingly, track retainer ring 257 can support track loop portion 256A in a first plane, and loop portion 256B in a second plane which is generally perpendicular to the first plane. Spokes 259 can be used to support retainer ring 257 on band 500. If desired, sheath 236 can be attached to retainer ring 257 if tracks 250A and 250B are supported to slide through ring 257 (eg. if tracks 250A and 250B pass through apertures in ring 257.)

In yet another embodiment, track 250 can comprise a wire or other suitable track piece having no distinct ends (i.e. no ends 252/254), but instead may comprise a smooth, uninterrupted track having a closed configuration (e.g. race track, oval, etc.) with a loop portion of the closed configuration track extending through the flexible member 230 to extend distally of the distal end 234 of the flexible member 230, and another loop portion of the closed configuration extending proximally of the handpiece 220. In such an embodiment, the loop portion extending proximally of the handpiece 220 can be manipulated by hand or by a controller to advance the loop portion distal of the flexible member 230 within the body lumen.

In each of the embodiments, it will be understood that one or more seals may be provided, as desired, to restrict gas or liquid flow through or around the flexible member 230, such as from a point outside the patient to a point within the lumen, especially if there is a desire to provide vacuum at the distal end of flexible member 230, or to otherwise isolate conditions in the lumen from conditions outside the lumen. For instance, with reference to FIGS. 11 and 12, it may desirable to provide a seal in association with guide tracks 242 and 244, and in channel 800 to prevent air from passing through the guide tracks or the channel 800. Seals for channels can be in the form of a small, flexible silicone rubber boot having an aperture through which a track 250 or instrument 900 can pass. Similarly, a flexible cuff or collar can be positioned over the flexible member 230 and can provide a seal between the flexible member 230 and the portion of the patient's body adjacent the opening to the patient's lumen. Lubricating gels and other lubricating products can also be utilized to enhance or provide sealing.

While various embodiments of the present invention have been disclosed, it will be obvious to those skilled in the art that such embodiments are provided by way of example only. The present invention may be provided in kit form with other medical devices, including medical devices useful in the working channel, and the kit elements can be pre-sterilized and packaged in a sealed container or envelope to prevent contamination. The present invention may be provided as a single use disposable device, or alternatively, may be constructed for multiple uses. Further, each element or component of the present invention may be alternatively described as a means for performing the function or functions performed by the element or component. Numerous variations, changes, and substitutions will now occur to those skilled in the art without departing from the invention. Accordingly, it is intended that the invention be limited only by the spirit and scope of the appended claims.

What is claimed is:

1. An endoscope for the gastrointestinal tract, comprising:
 a) a flexible elongate member comprising a proximal end and a distal end, the flexible elongate member further comprising a guide tube having an opening adjacent the distal end projecting at an oblique angle relative the longitudinal axis of the flexible elongate member;
 b) a visualization device and light source positioned adjacent the distal end of the flexible elongate member;
 c) a working channel extending between the proximal and distal ends of the flexible elongate member adapted to receive medical instruments, the working channel comprising an opening adjacent the distal end of the flexible elongate member; and
 d) a guide wire slidably received by the guide tube, the guide wire positioned between the proximal and distal ends of the flexible elongate member and extending distally relative the flexible elongate member to form a loop disposed distally relative the flexible elongate member, the guide wire being longitudinally moveable relative the flexible elongate member to vary the size of the loop.

2. The endoscope of claim 1, wherein the guide wire loop has a first end attached to the distal end of the flexible elongate member and a second end extending from the guide tube.

3. The endoscope of claim 1, wherein the flexible elongate member further comprises a second guide tube slidingly receiving the guide wire.

4. The endoscope of claim 3, wherein the guide wire loop has a first end extending from the guide tube and a second end extending from the second guide tube.

5. The endoscope of claim 3, wherein the second guide tube has an opening adjacent the distal end projecting at an oblique angle relative the longitudinal axis of the flexible elongate member.

6. The endoscope of claim 1, wherein the guide wire comprises a longitudinal wire core surrounded by a coil.

7. The endoscope of claim 1, wherein a proximal portion of the guide wire extends proximally from the flexible elongate member.

8. The endoscope of claim 7, further comprising a motor operable connected to the proximal portion of the guide wire to longitudinally move the guide wire relative the flexible elongate member.

9. The endoscope of claim 8, further comprising a control unit operable connected to the motor.

10. The endoscope of claim 7, wherein manual pushing and pulling of the proximal portion of the guide wire varies the size of the loop.

11. The endoscope of claim 1, further comprising a hand piece connected to the proximal end of the flexible elongate member.

12. The endoscope of claim 1, wherein the flexible elongate member has a length greater than 36 inches.

13. The endoscope of claim 1, wherein the flexible elongate member has an outer diameter between about 0.1 and about 1.0 inches.

14. The endoscope of claim 1, wherein the flexible elongate member further comprises a second guide tube having an opening adjacent the distal end of the flexible elongate section.

15. The endoscope of claim 14, wherein the guide wire further comprises a first proximal portion extending proximally relative the proximal end of the flexible elongate member, a first longitudinally section slidingly received by the guide tube, a distal section extending between the openings of the guide tube and second guide tube defining the loop, a second longitudinal section slidingly received by the second guide tube, and a second proximal portion extending proximally relative the proximal end of the flexible elongate member.

16. An endoscope, comprising:
   a) a flexible elongate member comprising a proximal end and a distal end;
   b) a visualization device and light source positioned adjacent the distal end of the flexible elongate member;
   c) first and second guide tubes each having an opening adjacent the distal end of the flexible elongate member, the guide tube openings project distally at an oblique angle relative the longitudinal axis of the flexible elongate member; and
   d) a guide wire received in the first and second guide tubes and extending from the openings to form a loop disposed distally relative the flexible elongate member, the guide wire being independently slideable in the first and second guide tubes to adjust the size of the loop.

17. The endoscope of claim 16, further comprising one or more motors operably connected to the guide wire to selectively move the guide wire in one or both guide tubes in the longitudinal direction.

18. The endoscope of claim 16, further comprising a working channel extending between the proximal and distal ends of the flexible elongate member adapted to receive medical instruments, the working channel comprising an opening adjacent the distal end of the flexible elongate member.

19. An endoscope, comprising:
   a) a flexible elongate member comprising a proximal end and a distal end;
   b) a visualization device and light source positioned adjacent the distal end of the flexible elongate member;
   c) first and second guide tubes each having an opening adjacent the distal end of the flexible elongate member;
   d) a guide wire received in the first and second guide tubes and extending from the openings to form a loop disposed distally relative the flexible elongate member, the guide wire being independently slideable in the first and second guide tubes to adjust the size of the loop; and
   e) one or more motors operably connected to the guide wire to selectively move the guide wire in one or both guide tubes in the longitudinal direction.

20. The endoscope of claim 19, wherein the guide tube openings project distally at oblique angle relative the longitudinal axis of the flexible elongate member.

21. The endoscope of claim 19, further comprising a working channel extending between the proximal and distal ends of the flexible elongate member adapted to receive medical instruments, the working channel comprising an opening adjacent the distal end of the flexible elongate member.

22. An endoscope for the gastrointestinal tract, comprising:
   a) a flexible elongate member comprising a proximal end and a distal end;
   b) a visualization device and light source positioned adjacent the distal end of the flexible elongate member;
   c) a working channel extending between the proximal and distal ends of the flexible elongate member adapted to receive medical instruments, the working channel comprising an opening adjacent the distal end of the flexible elongate member;
   d) a guide wire positioned between the proximal and distal ends of the flexible elongate member and extending distally relative the flexible elongate member to form a loop disposed distally relative the flexible elongate member, the guide wire being longitudinally moveable relative the flexible elongate member to vary the size of the loop, the guide wire comprising a proximal portion extending proximally from the flexible elongate member; and
   e) a motor operably connected to the proximal portion of the guide wire to longitudinally move the guide wire relative the flexible elongate member.

23. The endoscope of claim 22, wherein the flexible elongate member further comprises a first guide tube slidingly receiving the guide wire.

24. The endoscope of claim 23, wherein the flexible elongate member further comprises a second guide tube slidingly receiving the guide wire.

25. The endoscope of claim 24, wherein first or second guide tube has an opening adjacent the distal end projecting at an oblique angle relative the longitudinal axis of the flexible elongate member.

* * * * *